United States Patent
Nerbonne et al.

(10) Patent No.: US 7,686,279 B2
(45) Date of Patent: Mar. 30, 2010

(54) NON-REOPENABLE CLAMP FOR TUBING SETS

(75) Inventors: Karen Melissa Nerbonne, Lakewood, CO (US); Jeffrey Lee Spray, Erie, CO (US)

(73) Assignee: CaridianBCT, Inc., Lakewood, CO (US)

( * ) Notice: Subject to any disclaimer, the term of this patent is extended or adjusted under 35 U.S.C. 154(b) by 569 days.

(21) Appl. No.: 11/612,625

(22) Filed: Dec. 19, 2006

(65) Prior Publication Data

US 2007/0261214 A1   Nov. 15, 2007

Related U.S. Application Data

(60) Provisional application No. 60/800,128, filed on May 12, 2006.

(51) Int. Cl.
*F16K 7/04* (2006.01)

(52) U.S. Cl. .................. 251/10; 251/4; 251/9; 604/250

(58) Field of Classification Search .................. 251/4, 251/9, 10; 24/326; 604/250
See application file for complete search history.

(56) References Cited

U.S. PATENT DOCUMENTS

| | | | | |
|---|---|---|---|---|
| 823,068 | A | * | 6/1906 | Mosley .................. 251/10 |
| 3,247,852 | A | * | 4/1966 | Schneider .................. 606/120 |
| 3,698,681 | A | * | 10/1972 | Lacey .................. 251/10 |
| 3,822,052 | A | | 7/1974 | Lange |
| 3,900,184 | A | | 8/1975 | Burke et al. |
| 3,942,228 | A | | 3/1976 | Buckman et al. |
| 4,053,135 | A | | 10/1977 | Saliaris |
| 4,091,815 | A | | 5/1978 | Larsen |
| 4,112,944 | A | | 9/1978 | Williams |
| 4,193,174 | A | | 3/1980 | Stephens |
| 4,235,412 | A | | 11/1980 | Rath et al. |
| 4,453,295 | A | | 6/1984 | Laszczower |
| 4,588,160 | A | | 5/1986 | Flynn et al. |
| 4,589,626 | A | | 5/1986 | Kurtz et al. |
| 4,643,389 | A | | 2/1987 | Eison et al. |
| 4,673,161 | A | | 6/1987 | Flynn et al. |
| 4,787,406 | A | | 11/1988 | Edwards et al. |
| 4,807,622 | A | * | 2/1989 | Ohkaka et al. .............. 606/167 |
| 5,035,399 | A | | 7/1991 | Rantanen-Lee |
| D325,631 | S | | 4/1992 | Daoud et al. |

(Continued)

FOREIGN PATENT DOCUMENTS

EP   0206997 A1   6/1986

(Continued)

OTHER PUBLICATIONS

PCT/US2006/062291: International Search Report and Written Opinion, Nov. 26, 2007.

*Primary Examiner*—John K Fristoe, Jr.
*Assistant Examiner*—Marina Tietjen
(74) *Attorney, Agent, or Firm*—Edna M. O'Connor; John R. Merkling; Laura B. Arciniegas

(57) ABSTRACT

A non-reopenable, single-use clamp for receiving and pinching collapsible resilient tubing thus forming a mechanical tubing seal and having an open position for insertion of tubing, a neutral position for holding the tubing and a closed position for non-reopenably closing the tubing with a locking mechanism with locking hooks.

17 Claims, 4 Drawing Sheets

U.S. PATENT DOCUMENTS

| | | | |
|---|---|---|---|
| 5,203,056 A | 4/1993 | Funk et al. | |
| 5,238,218 A | 8/1993 | Mackal | |
| 5,401,256 A | 3/1995 | Stone et al. | |
| 5,817,116 A * | 10/1998 | Takahashi et al. | 606/167 |
| D427,307 S | 6/2000 | Guala et al. | |
| 6,089,527 A | 7/2000 | Utterberg | |
| 6,113,062 A | 9/2000 | Schnell et al. | |
| D431,650 S | 10/2000 | Guala et al. | |
| 6,129,330 A | 10/2000 | Guala | |
| 6,161,812 A | 12/2000 | Guala et al. | |
| 6,196,519 B1 | 3/2001 | Utterberg | |
| 6,234,448 B1 | 5/2001 | Porat | |
| D465,843 S | 11/2002 | Guala | |
| 6,592,558 B2 * | 7/2003 | Quah | 604/250 |
| 6,644,618 B1 | 11/2003 | Balbo | |
| 6,742,760 B2 * | 6/2004 | Blickhan et al. | 251/11 |
| 7,234,677 B2 * | 6/2007 | Zerfas | 251/10 |

FOREIGN PATENT DOCUMENTS

| | | |
|---|---|---|
| EP | 0206997 B1 | 6/1986 |
| EP | 0799627 A2 | 10/1997 |
| EP | 0995 461 B1 | 10/1998 |
| EP | 1000633 A2 | 5/2000 |
| EP | 1389473 A1 | 2/2004 |
| EP | 0995 462 B1 | 9/2004 |

* cited by examiner

NON-REOPENABLE CLAMP FOR TUBING SETS

PRIORITY CLAIM

This application claims the benefit of U.S. Provisional Patent Application No. 60/800,128 filed May 12, 2006

FIELD OF THE INVENTION

This invention relates generally to the field of tubing clamping devices, and in particular to a non-reopenable clamp for receiving collapsible resilient medical tubing.

BACKGROUND OF THE INVENTION

Clamps for receiving collapsible resilient tubing are well known and have been in use for a number of years. They hold an important role in controlling the flow of various fluids and gases transported in tubing, particularly medical tubing. The mode of operation for the majority of tubing clamps is to pinch the tubing in such a manner as to collapse the inner lumen of the tubing. Clamps that provide varying degrees of lumen collapse are used to regulate the flow of the fluids and gases through the tubing. Still other clamps are designed to allow either full flow through the tubing or to completely collapse the lumen to fully halt fluid or gas flow. Furthermore, the mechanism of closure in the majority of these clamps is reversible; that is to say, the clamp may be closed and opened multiple times as needed. However, in certain applications, particularly of a medical nature, a single-use clamp that for all intents and purposes is non-reopenable is desirable. That is, by non-reopenable is meant that once closed the clamp cannot be reopened under ordinary use without application of a major force that may destroy the clamp through its application.

Tubing is widely used in many scientific, industrial, and medical applications. This tubing is typically a component of more complex assemblies that include disposable sets for apheresis systems, renal dialysis systems, and other medical devices. These disposable sets are typically pre-manufactured and assembled with various other components including bags, filters, and needles interconnected by the tubing. By virtue of their design, many of the clamps in current-day use require the tubing to be threaded through the clamp prior to the addition of the afore-mentioned components. This design and assembly process is necessary to ensure that the clamp remains in the predetermined location on the disposable set throughout sterilization, packaging, transportation, and final use and to ensure that the tubing remain in a proper orientation for clamp closure and subsequent tube sealing.

The process of use for many of the disposable sets requires the user to disconnect one or more sub-assemblies from the whole disposable set during or after the procedure. This act typically requires the sealing of the tubing leading to this sub-assembly to ensure a complete seal. Conventional practice is to use a radio frequency welder to collapse and, by virtue of radio frequency-generated heat, bond the tubing's inner lumen to create a complete seal. As a supplemental measure of safety, a clamp of conventional design may also be engaged on the tubing to create an additional, non-permanent or reopenable seal.

In certain countries however, governmental regulations pertaining to blood collection and other medical procedures have dictated that while the aforementioned disposable set is connected to a patient, or donor of blood, typically by means of one or more needles, a radio frequency welder may not be used to seal any tubing. These regulations have created a need for a mechanical means or method of sealing the tubing in a non-reopenable manner. Furthermore, since the medical or blood collection practitioner determines at which location the tubing is to be sealed, a need for a clamp that may be inserted onto the tubing or relocated from the assembled location post-manufacture also exists.

U.S. Pat. No. 6,644,618 to Balbo discloses a fast-fit clamp for regulating flow along flexible tubing, in particular for medical use. This clamp possesses two holes facing outwards to allow edgewise insertion and removal of tubing into the clamp. U.S. Design Pat. No. D465,843 to Guala further discloses a clamp for flexible medical lines.

A need exists for a clamp that may be easily placed on the tubing during or after the disposable set assembly process, remain in contact with the tubing throughout sterilization, packaging, transportation, and other handling procedures, and for non-reopenably sealing in a mechanical manner a given section of tubing.

SUMMARY OF THE INVENTION

In one aspect, the present invention is a non-reopenable clamp for receiving collapsible resilient medical tubing that includes a first plate and a second plate joined by a connector mechanism. Further in accordance with this aspect of the invention, a non-reopenable locking mechanism is provided on the clamp which is composed of one or more hooks located on one or more protrusions which engage a latching mechanism and form a non-reopenable lock or locking mechanism to cooperatively seal associated tubing.

The present invention is also directed at methods for inserting and holding the tubing in the non-reopenable clamp and for forming a mechanical seal on such tubing. In another aspect of the present invention, the method includes applying an external force to open the clamp from a neutral position to facilitate the insertion of a given length of tubing into the clamp prior to mechanically sealing the tubing. The method further includes the removal of the external force to return the clamp to the neutral position, which by virtue of the various clamp elements and their relative positions, maintains the clamp on the tubing throughout various handling procedures including sterilization, packaging, and transportation. The method further includes the application of an external force to close the clamp and to form a non-reopenable mechanical seal by collapsing the inner lumen of the tubing thereby halting or preventing any fluid or gas flow.

DESCRIPTION

The present invention relates to a non-reopenable, single-use clamp 1, generally designated in FIGS. 1-7. The non-reopenable clamp 1 is for receiving and pinching a given length of collapsible resilient tubing 100, generally designated in FIGS. 4-7, to form a mechanical tubing seal or to fully occlude the tubing 100. By single use is meant that the clamp 1 cannot be opened and reused under ordinary use once it is locked or closed. That is, the clamp 1 can only be locked or closed on tubing a single time during ordinary use as the clamp 1 is non-reopenable. By non-reopenable it is meant that the clamp once closed cannot be opened or reopened under ordinary use without application of a major force that may destroy the clamp by its application.

The clamp 1 is made from a polymer suitable for medical applications and preferably resistant to failure upon undergoing sterilization procedures common to the medical industry. Clamp 1 is preferably of unitary construction and typically injection molded as an integral device. Although the method of manufacture of injection molding and polymer composition are disclosed, other suitable materials and manufacturing processes known to one skilled in the art are also contemplated by the present invention. By way of example, though not to be limiting, the clamp 1 may be constructed of various metals, though this may not be as economically advantageous as polymer construction.

Specific reference will now be made to the figures and throughout all the figures, same elements are numbered in an identical manner.

Figure 1:
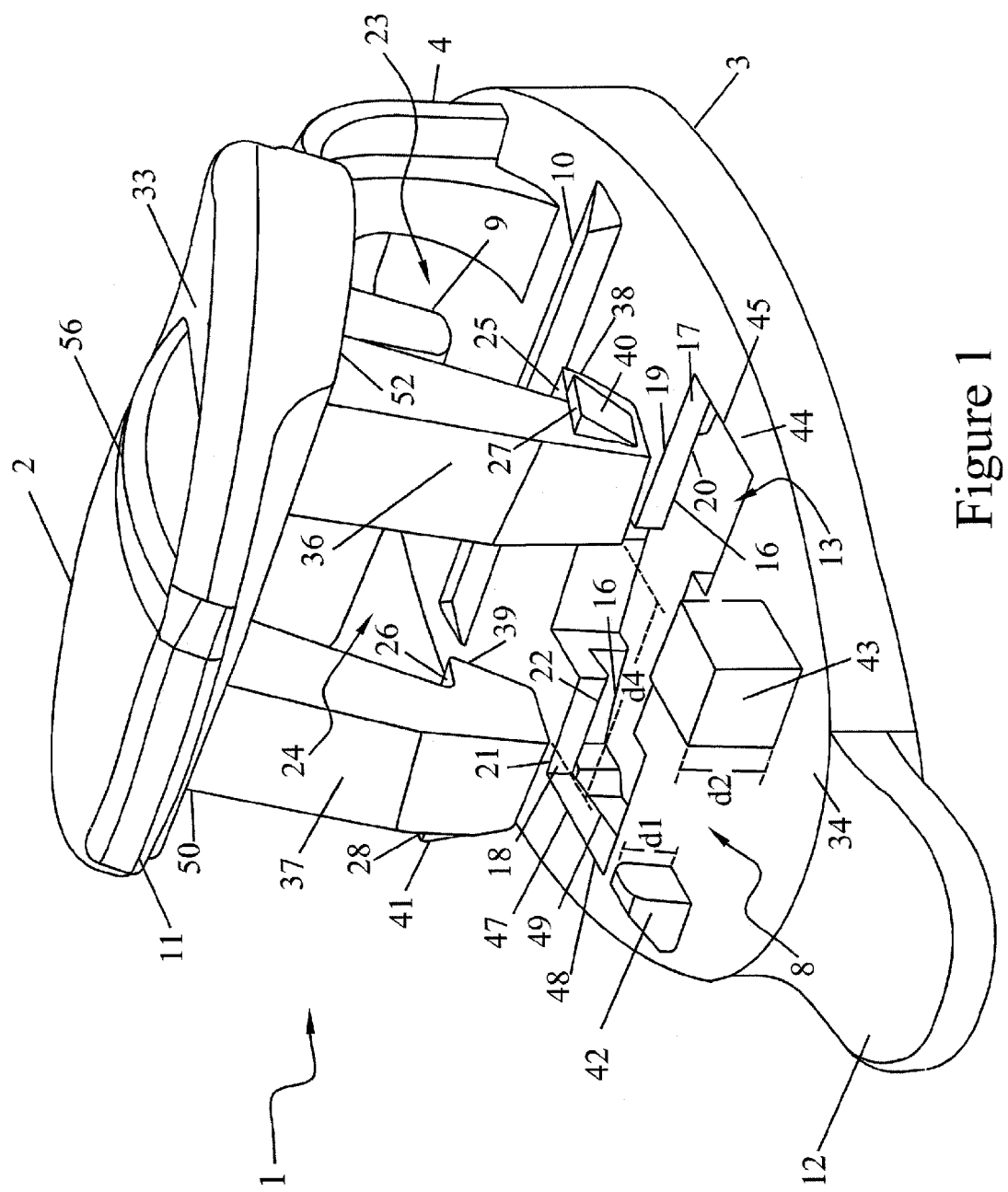
FIG. 1 depicts a perspective view of the non-reopenable, single-use clamp in the neutral position without tubing.
Figure 3:
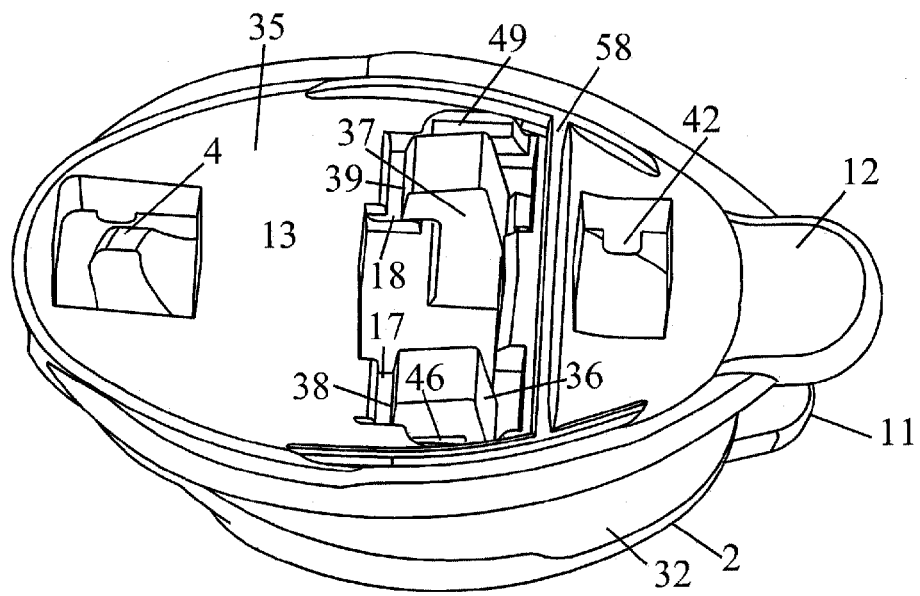
FIG. 3 depicts a perspective view of the clamp from a bottom view detailing the non-reopenable locking mechanism in the closed position.

With reference to FIG. 1, clamp 1 comprises a plate 2 and a plate 3. Plate 2 further comprises a surface 32, shown in FIG. 3, and surface 33; plate 3 further comprises a surface 34 and surface 35, (FIG. 3). Plate 2 and plate 3 are joined by a connector such as a single point hinge 4. Both the plates 2 and 3 are shown in the figures as being substantially of oval shape, although other shapes or combinations thereof would not adversely affect the operation of the clamp 1 and are contemplated by the present invention.

Figure 2:
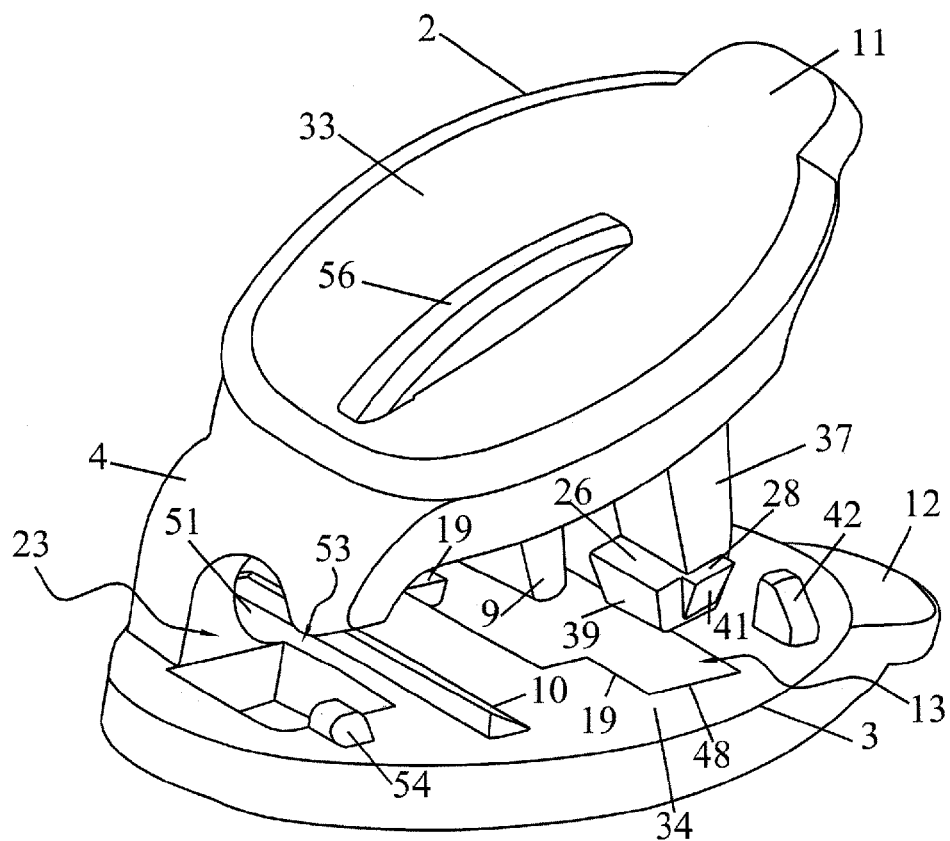
FIG. 2 depicts another perspective view of the non-reopenable, single-use clamp again in the neutral position.

Continuing in reference to FIGS. 1-3, disposed on and in a relatively perpendicular manner to surface 32 is a protrusion 36 having a substantially rectangular cross-section and a protrusion 37 also having a substantially rectangular cross-section. Protrusion 36 and protrusion 37 are attached or in intimate contact with surface 32 at ends 52 and 50 respectively. Opposite end 52 of protrusion 36 is a hook 38 and a hook 40. Opposite end 50 of protrusion 37 is a hook 39 and a hook 41. Hook 38 has top surface 25 and hook 40 has top surface 27. Similarly, on protrusion 37 book 39 has top surface 26 and hook 41 has top surface 28.

In the present embodiment, protrusions 36 and 37 are substantially rectangular in cross section although other cross sectional shapes such as circular, square, or triangular could be incorporated into the clamp's design. The hooks 38, 40, 39 and 41 generally increase in cross-section as they extend toward surfaces 25, 27, 26 and 28 respectively for the sliding movement as will be described in more detail below.

Figure 5:
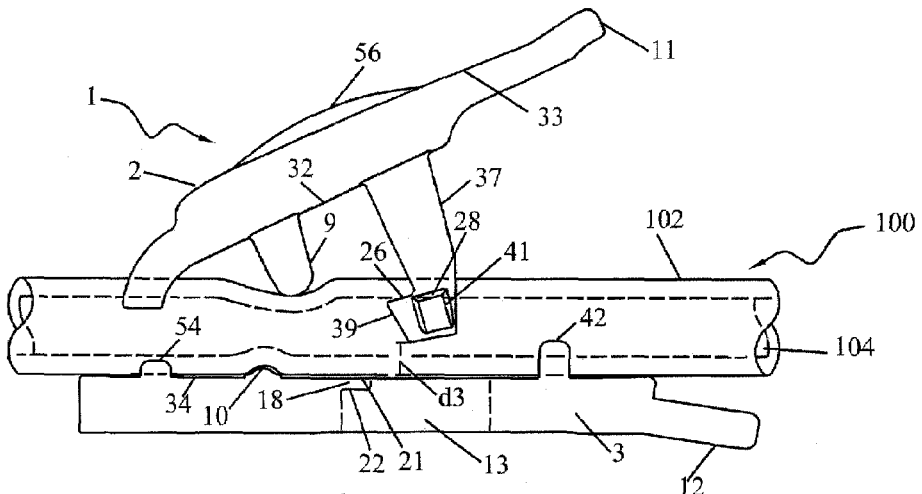
FIG. 5 depicts a side view of the clamp in the neutral position with associated tubing.

In reference to FIG. 1 and FIG. 5, further disposed on plate 2 is a rib 9 which is integrally connected to surface 32 in a relatively perpendicular manner. Also disposed on plate 2 is a finger locator tab 11 where plate 2 and finger locator tab 11 may cooperatively form a continuous element. Finger locator tab 11 is preferably located towards the front or the side of plate 2 opposite the single point hinge 4. Finger locator tab 11 is provided to afford the user additional leverage when applying a closure force. An alternate embodiment may eliminate finger locator tab 11 without seriously affecting the operation of clamp 1.

Ridge 56 is also provided on plate 2. This ridge 56 is raised from surface 33 of plate 2 to direct the finger or thumb tip of the operator of the clamp 1 toward locator 11 by causing an uncomfortable pressure on the finger or thumb pressing on ridge 56. Using finger locators 11, 12 allow the operator to more easily apply sufficient pressure to press clamp 1 into the locked or closed position as more fully described below and shown in FIG. 6.

In reference to FIG. 1, disposed on surface 34 of plate 3 is a tubing locator guide 8 which includes a protrusion 42 and a protrusion 43 disposed substantially perpendicular to surface 34. Protrusion 42 extends a distance d1 from surface 34 of plate 3 and protrusion 43 extends a distance d2 from surface 34 of plate 3. Although d1 and d2 can be of any length, depending on the size of the clamp 1 and tubing 100, d1 is shown as a shorter length than d2 to advantageously allow the lateral insertion of the tubing 100 in a direction towards protrusion 43 and for the tubing 100 to seat against protrusion 43. Lateral insertion is defined as the approach of tubing 100 towards clamp 1 from the side of clamp 1 or towards the single point hinge 4 and protrusion 43. During lateral insertion tubing 100 is placed between plate 2 and plate 3. The combination of protrusion 42 and protrusion 43 serve to centrally locate the tubing in a preferential orientation to facilitate clamp 1 closure. Other configurations, not shown, may be used to locate the tubing 100 between plates 2 and 3. The only requirement is that the tubing 100 be restrained even when clamp 1 is open.

Although lateral insertion of tubing 100 is shown from one side in the figures, it is understood the clamp 1 structure could be reversed to permit lateral insertion of tubing from the other side.

Disposed on plate 3 is an aperture 13 providing access to and incorporating a shape to preferentially accept protrusion 36 and protrusion 37 and provide latching mechanism 16. Latching mechanism 16 incorporates a shelf 17, a shelf 18, a shelf 44 and a shelf 47 to engage hooks 38, 39, and 40, 41, respectively, as shown in FIG. 1. The structure of shelf 17 further comprises a top edge 19, and a bottom edge 20; the structure shelf 18 further comprises a top edge 21 and a bottom edge 22; the structure of shelf 44 further comprises a top edge 45 and a bottom edge 46 shown in FIG. 3; and the structure of shelf 47 further comprises a top edge 48 and a bottom edge 49. The locking and latching operation will be further described below.

With reference to FIG. 2, plate 3 further incorporates a rib 10 which is integrally connected to surface 34 in a relatively perpendicular manner. Disposed on plate 3 is a finger locator tab 12 preferably located towards the front of the plate 3 opposite single-point hinge 4. Finger locator tab 12 is provided to afford the user additional leverage when applying a closure force. An alternate embodiment may eliminate this tab without seriously affecting the operation of clamp 1. Finger locator tab 12 may be formed continuous to plate 3. Also similar to ridge 56 on plate 2, ridge 58 (shown in FIG. 3) directs the finger or thumb toward finger locator 12.

With reference to FIG. 1, single-point hinge 4 connects plate 2 and plate 3 and maintains them at an angle and distance relative to each other in the neutral position as described below. The neutral position of the clamp corresponds to the normal or relaxed position of the hinge 4. By single-point hinge 4 is meant a hinge which connects plate 2 and plate 3 together at one location so as to not block the insertion of tubing 100 between plates 2 and 3. With reference to FIG. 2, single point hinge 4 incorporates a further tubing locator guide 23 incorporating a through-hole 51 in the hinge 4 and of such diameter as to intimately contact the outside wall of inserted tubing 100 as shown in FIG. 5; and an open slotted side 53 on hinge 4 in direct communication with the through-hole 51 to facilitate the insertion of tubing in a lateral manner into tubing locator guide 23. Protrusion 54 helps locate tubing 100 in through-hole 51 to prevent tubing 100 from being dislodged when it has been laterally inserted into the through-hole.

Figure 4:
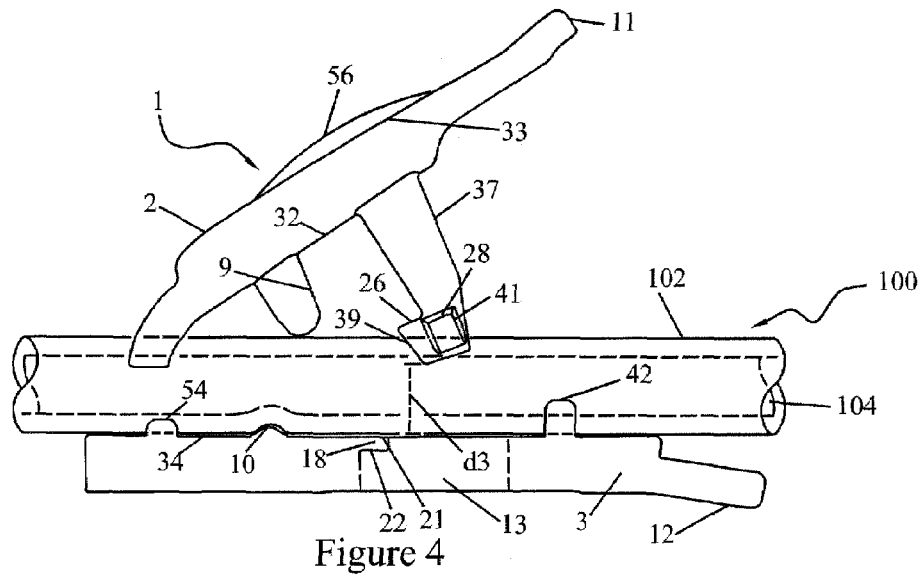
FIG. 4 depicts a side view of the clamp in the open position with associated tubing.
Figure 6:
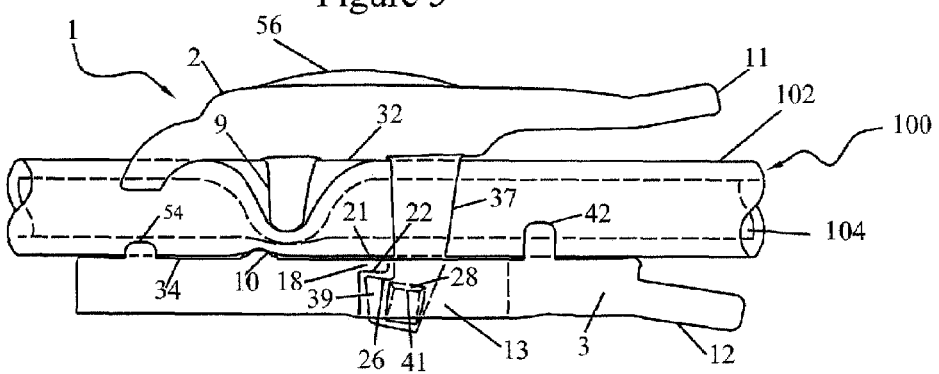
FIG. 6 depicts a side view of the clamp in the closed position with associated tubing.

The following three clamp positions as shown in FIGS. 4-6 are hereby defined and contemplated by the present invention. Firstly, FIG. 4 depicts clamp 1 in an open position. To place the clamp 1 in the open position an external force must be applied to plate 2 and plate 3 either directly or by way of finger locator tab 11 and finger locator tab 12. Plate 2 and plate 3 are consequently manually moved apart from each other by the user and correspondingly, distance d3 depicted in FIGS. 4 and 5 is increased to a point sufficient to allow the lateral insertion of the tubing 100 to rest between protrusions 42 and 43. This open position of the clamp 1 corresponds to an expanded or open position of single point hinge 4. The open position of the clamp 1 provides an opening between rib 9 and rib 10 for lateral insertion of the tubing 100. This lateral movement also guides the tubing into second locator guide 23 over protrusion 54. In the open position of the clamp, the inner lumen 104 of tubing 100 remains open.

FIG. 5 depicts clamp 1 in a neutral position or rest position. The neutral position is defined as the angle and distance of plate 2 and plate 3 relative to each other when there is an absence of an applied external force. In the neutral position, also shown in FIG. 1, clamp 1 provides a channel 24 formed cooperatively by protrusions 42 and 43, the through-hole of tubing locator guide 23, and by protrusions 36 and 37. These protrusions 36 and 37 form distance d4, where d4 is defined in FIG. 1 as the spacing between protrusion 36 and protrusion 37. In the neutral position, distance d3, depicted in FIG. 5, is substantially minimized so as to prevent the inadvertent removal or separation of the tubing 100 from channel 24 and inherently, from clamp 1. In the neutral position rib 9 and rib 10 make contact with outer wall 102 of tubing 100. However, the contact between ribs 9 and 10 is sufficient to hold the tubing 100 in place but not sufficient enough to cause full collapse of inner lumen 104 of tubing 100. The neutral position of the clamp corresponds to the normal or relaxed position of the hinge 4.

Lastly, FIG. 6 depicts clamp 1 in a closed position. To place the clamp 1 in the closed position an external force must be applied to plate 2 and plate 3 either directly or by way of finger locator tab 11 and finger locator tab 12. In the closed position, plate 2 and plate 3 are moved substantially towards each other and single point hinge 4 is in a closed or compressed position. During the movement of plates 2 and 3 toward the closed position, hook 38 disposed on the end of protrusion 36 initially contacts edge 19 of shelf 17 and slides or moves along such shelf 17. During the sliding movement, protrusion 36 is biased away from its rest position. The hook 38 slides along the shelf 17 until top surface 25 of hook 38 slips under bottom edge 20 and moves thus under shelf 17 during the movement of plates 2 and 3 towards each other. Hook 40, also disposed on the end of protrusion 36, initially contacts top edge 45 of shelf 44 to slide or move along shelf 44 until the top surface 27 of 40 slips under bottom edge 46. Similarly, hook 39 moves to engage top edge 21 of shelf 18 to slide or move along shelf 18 until surface 26 slips under bottom edge 22. In a manner similar to hook 40, hook 41 slips under bottom edge 49 of shelf 47 (shown in FIG. 1). Once the hooks 38, 40, and 39, 41 and the shelves 17, 44, 18, 47 are respectively engaged, clamp 1 is non-reopenable under normal circumstances and is not reusable. The biasing action against the rest location of the protrusions 36, 37 during movement assure that the hooks 38, 40, 39, and 41 effectively spring under the respective ledges or shelves 17, 44, 18, 47 to make reversal of the locking mechanism difficult. Since each protrusion has two hooks, it is even more difficult to bias the protrusion so that the hooks can be released. The primary locking action may be accomplished by hooks 38 and 40 but the additional hooks 39 and 41 aid in the clamp being non-reopenable.

With reference to FIG. 6, it is in the closed position that rib 9 and rib 10 are placed in intimate contact with tubing 100. By virtue of the dimensions of rib 9 and rib 10, the tubing 100 is subjected to a constant force from two sides in such a manner as to collapse the inner lumen 104 of the tubing, thus halting or preventing any and all fluid or gas flow.

The structure of clamp 1 allows the clamp 1 to be placed on tubing 100 prior to final use which could be at the time of manufacture. Thus the clamp 1 can be provided on assemblies such as the disposable set 70 shown in FIG. 7 and discussed below. With reference to FIG. 1 and FIG. 5, when clamp 1 is in the neutral position, channel 24, protrusions 42 and 43, protrusions 36 and 37, and locator guide 23 as well as rib 9, and rib 10, previously described, maintain the clamp 1 in contact with the tubing 100 throughout sterilization, packaging, transportation, and other handling procedures until such a time as the user desires to place the clamp 1 in the closed position. Also, clamp 1 with open slotted side 53, the tubing locator guide 23 and channel 24 permit the tubing 100 to be laterally inserted so that the clamp 1 may also be placed on the tubing 100 post-manufacture. In addition, any clamp 1 found to be defective or damaged may be easily replaced by the user.

Although specific tubing locator guides, such as protrusions 42 and 43 are shown, it is understood that such locator guides may comprise a rib, a through-hole or an open slotted side. Also, concerning the relative movement of plates 2 and 3 it is understood that only one plate 2 or 3 would need to be moved if the other plate was fixed against a hard surface.

Figure 7:
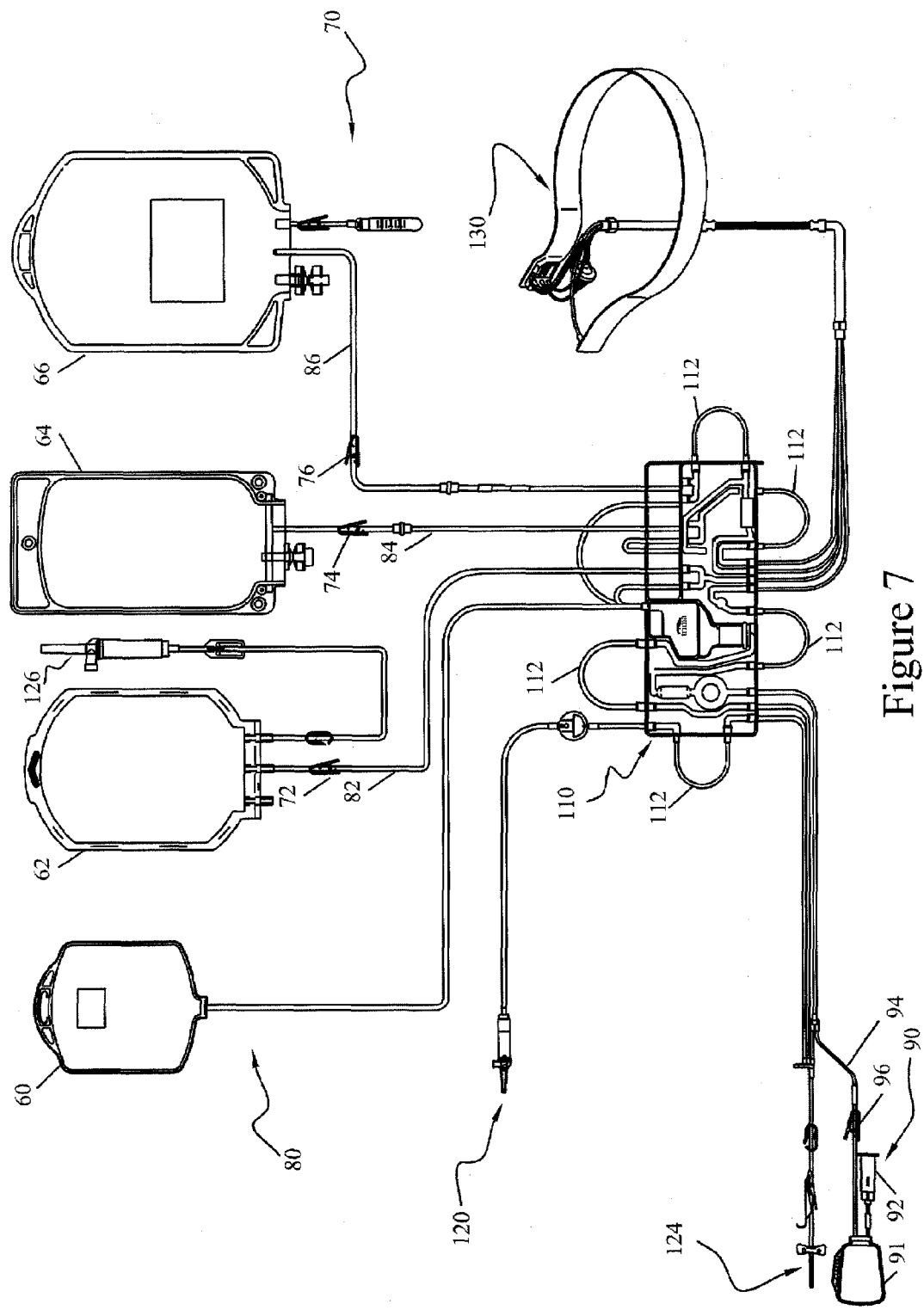
FIG. 7 depicts an overall view, not to scale, of a disposable set used in an apheresis system with the clamps as shown in FIGS. 1-6.

FIG. 7 shows a typical disposable set 70 for use on an apheresis machine. The disposable or tubing set 70 includes a separation vessel 130 for separating blood into various blood components. The set 70 includes a fluid flow cassette 110 having peristaltic pump loops 112, a receive and return line 124 for receiving and returning blood or blood components to or from a donor, an anticoagulant line 120 for adding anticoagulant to blood from the donor, and a gas line 80 for receiving, into bag 60, gas purged from the system.

Various collection lines and bags for blood components may also be part of the disposable set 70 and will be more fully described later.

A sample set 90 may also be part of the disposable set 70. The sample set 90 includes line or conduit 94 through which a blood sample fluidly flows to sample bag 91. A blood sample may then be retrieved through sample device 92. A clamp 96 similar to clamp 1, shown in FIGS. 1-6, may be placed on line or conduit 94. Such a non-openable clamp 96 would assure the sample set 90 could be isolated from the disposable system 70 and the donor before a sample is taken. This is important to maintain the closed system disposable set.

Similarly, the clamp 1 of the instant invention can be used for various product lines or conduits. Such a clamp 72 is shown on line or conduit 82 leading to red blood cell bag 62. A connection for storage solution for any collected or packed red blood cells is shown at 126.

The plasma line 84 leading to plasma bag 64 has clamp 74, also described as clamp 1 of the instant invention, and platelet line 86 may also have similar clamp 76 to isolate platelet bag 66.

The above shows examples of uses of the clamp 1 of the instant invention. It is understood that similar clamps may be used on any tubing sets as well as for other uses involving medical or collapsible tubing as needed. It is further understood that such clamps may be useful on a variety of apheresis tubing as well as whole blood collection tubing. FIG. 7 illustrates only a few possibilities for the clamp of the instant invention. The clamp of the instant invention is appropriate for any tubing where a secure and non-reopenable mechanism or method is needed to close collapsible tubing.

The embodiments of the present invention have been described by reference to a non-reopenable, single-use clamp for receiving and pinching a given length of collapsible resilient tubing to form a mechanical tubing seal. It should be understood that the present invention is not so limited. The present invention may be used in a variety of medical and non-medical circumstances where it is desirable to form a mechanical seal in any type of collapsible tubing. Present embodiments of the present invention and many of its aspects, features and advantages have been described with a degree of particularity. It should be understood that this description has been made by way of example, and that the invention is defined by the scope of the following claims.

What is claimed is:

1. A non-reopenable clamp for receiving collapsible resilient tubing comprising:
    a first plate;
    a second plate wherein the collapsible resilient tubing is received between said first and second plates;
    a non-reopenable locking mechanism comprising:
        a first hook extending from one of said first or second plates;
        a second hook extending from one of said first or second plates;
        a third hook extending from one of said first and second plates;
        a fourth hook extending from one of said first and second plates;
        at least one latching mechanism on the other of said first or second plates for securing the collapsible tubing from opening comprising:
            a first shelf for engaging said first hook;
            a second shelf for engaging said second hook;
            a third shelf for engaging the third hook; and
            a fourth shelf for engaging the fourth hook wherein said clamp is non-reopenable when said first, second, third and fourth hooks are engaged respectively by said first, second, third and fourth shelves.

2. The non-reopenable clamp of claim 1 wherein:
    said clamp is formed of molded polymer.

3. The non-reopenable clamp of claim 1 wherein said non-reopenable locking mechanism comprises:
    a first protrusion extending from one of said first and second plates wherein said first and second hooks are disposed on said first protrusion.

4. The non-reopenable clamp of claim 1 wherein one of said first or second plates further comprises:
    a first rib for positively engaging the collapsible resilient tubing.

5. The non-reopenable clamp of claim 3 comprising:
    a first rib for positively engaging the collapsible resilient tubing wherein said first rib is disposed on said same first or second plate on which is disposed said first protrusion.

6. The non-reopenable clamp of claim 1 comprising:
    a first tubing locator guide disposed on one of said first or second plates comprising:
        a first guide protrusion disposed substantially perpendicular to said first or second plate; and
        a second guide protrusion disposed substantially perpendicular to said first or second plate.

7. The non-reopenable clamp of claim 1 further comprising:
    a connector connecting said first and second plates.

8. The non-reopenable clamp of claim 4 wherein said first or second plate further comprises:
    a second rib for positively engaging collapsible resilient tubing;
    said second rib disposed perpendicular to said first or second plate and offset along said axis from said first rib.

9. The non-reopenable clamp of claim 8 wherein:
    said second rib is disposed on the plate opposite said first or second plate on which is disposed said first rib.

10. The non-reopenable clamp of claim 1 further comprising:
    a first finger locator tab on one of said first or second plates.

11. The non-reopenable clamp of claim 1 further comprising:
    a second finger locator tab on the other of said first or second plates.

12. The non-reopenable clamp of claim 7 wherein said connector further comprises:
    a single-point hinge.

13. The non-reopenable clamp of claim 12 wherein said single-point hinge further comprises:
    a tubing locator guide comprising a through-hole and an open sidewall.

14. The non-reopenable clamp of claim 3 wherein said non-reopenable locking mechanism further comprises:
    a second protrusion extending from one of said first or second plates wherein said third and fourth hooks are disposed on said second protrusion.

15. The non-reopenable clamp of claim 14 wherein:
    said first and second protrusions are disposed on said same first or second plate.

16. The non-reopenable clamp of claim 14 wherein:
    said first protrusion and said second protrusion form a channel for the collapsible resilient tubing.

17. A method of closing collapsible tubing in a non-reopenable manner comprising:
    providing a clamp on the tubing wherein the clamp has first and second hooks and third and fourth hooks;
    sliding the first and second hooks along respective first and second shelves;
    slipping the first and second hooks under their respective first and second shelves to engage the shelves;
    sliding the third and fourth hooks along respective third and fourth shelves; and
    slipping the third and fourth hooks under respective third and fourth shelves to engage the shelves wherein the clamp is latched in an non-openable manner.

\* \* \* \* \*